United States Patent [19]

Chu

[11] Patent Number: 4,699,473

[45] Date of Patent: Oct. 13, 1987

[54] TRIFLUOROMETHYL SUBSTITUTED SPIROOXAZINE PHOTOCHROMIC DYES

[75] Inventor: Nori Y. C. Chu, Shrewsbury, Mass.

[73] Assignee: American Optical Corporation, Southbridge, Mass.

[21] Appl. No.: 803,794

[22] Filed: Dec. 2, 1985

Related U.S. Application Data

[63] Continuation of Ser. No. 521,309, Aug. 8, 1983, abandoned, which is a continuation-in-part of Ser. No. 497,263, May 23, 1983, abandoned, which is a continuation-in-part of Ser. No. 360,455, Mar. 22, 1982, Pat. No. 4,440,672.

[51] Int. Cl.$^4$ ............... G03C 1/733; G02B 5/23; G02F 1/01; C07D 265/00
[52] U.S. Cl. .................. 350/409; 350/354; 430/345; 544/70; 544/71; 252/586
[58] Field of Search ............ 252/586; 350/354, 409; 430/345; 544/70, 71

[56] References Cited

U.S. PATENT DOCUMENTS

| | | | |
|---|---|---|---|
| 3,562,172 | 2/1971 | Ono et al. | 252/300 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,440,672 | 4/1984 | Chu | 252/586 |

FOREIGN PATENT DOCUMENTS

| | | | |
|---|---|---|---|
| 659801 | 6/1965 | Belgium | 252/300 |
| 1927849 | 12/1970 | Fed. Rep. of Germany | 544/71 |
| 49-53180 | 5/1974 | Japan | 252/586 |
| 85/02619 | 6/1985 | PCT Int'l Appl. | |

Primary Examiner—John F. Terapane
Assistant Examiner—Catherine S. Kilby
Attorney, Agent, or Firm—Dike, Bronstein, Roberts, Cushman & Pfund

[57] ABSTRACT

The organic photochromic composition of this invention comprises trifluoromethyl substituted spiro (indoline-2,3'-(3$\underline{H}$) napth-(2,1-b)(1,4)oxazine) (SO) dyes. This new class of (SO) photochromic compounds has a more neutral color when subjected to ultraviolet light irradiation.

When used with a photochromic plastic embodiment, these (SO) compounds give the plastic embodiment a high luminous transmittance in an unactivated state, which can be darkened significantly when subjected to ultraviolet light irradiation. When an ultraviolet stabilizer is used with the photochromic compositions of this invention, the light fatigue resistance of the (SO) dye is improved and it will not hinder the photocolorability of the photochromic composition.

32 Claims, 2 Drawing Figures

TRIFLUOROMETHYL SUBSTITUTED SPIROOXAZINE PHOTOCHROMIC DYES

CROSS-REFERENCE TO RELATED APPLICATIONS

This application is a continuation of application Ser. No. 521,309, filed Aug. 8, 1983, now abandoned, which is a continuation-in-part application of U.S. Ser. No. 497,263 filed May 23, 1983, now abandoned entitled Photochromic Composition Resistant to Fatigue; which is a continuation-in-part application of U.S. Ser. No. 360,455, filed Mar. 22, 1982, now U.S. Pat. No. 4,440,672 entitled Photochromic Composition Resistant to Fatigue, the teachings of which are both incorporated herein by reference.

BACKGROUND OF THE INVENTION

The invention relates to a photochromic composition, and more particularly to an organic photochromic composition comprising spiro (indoline-2,3'-(3H)-napth-(2,1-b)(1,4) oxazine)(SO) dye, with substitution of a trifluoromethyl group in the indoline part of the molecule.

As used throughout this specification and claims, the terms (SO) dye, (SO) compound or (SO) derivative are intended to represent a compound having the following structural formula:

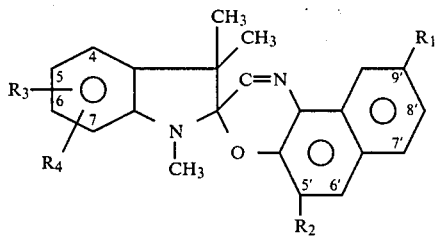

wherein "SO" is an abbreviation for spiro (indoline-2,3'-(3H)-napth(2,1-b)(1,4) oxazine), and hereinafter the parent compound is a (SO) compound wherein $R_1$, $R_2$, $R_3$ and $R_4$ are hydrogen.

Compounds which undergo reversible photo-induced color changes are termed photochromic compounds. When subjected to ultraviolet light or visible irradiation, these photochromic compounds change their transmission. They subsequently revert to their original color state when they are subjected to a different wavelength of radiation or when the initial light source is removed.

The photochromism of (SO) compounds was first disclosed in U.S. Pat. Nos. 3,562,172 and 3,578,602. These compounds are (SO) derivatives with substitutions in the indoline part of the molecule. Subsequently, U.S. Pat. Nos. 4,215,010 and 4,342,668 disclosed (SO) derivative compounds with substitution in the naphthalene part of the molecule in addition to substitution in the indoline part of the molecule. These (SO) derivative compounds in the two latter patents show an enhanced photocolorability when compared to the (SO) derivative compounds disclosed in U.S. Pat. Nos. 3,562,172 and 3,578,602.

A solution of all (SO) derivative compounds in common organic solvents, as disclosed in the four above-mentioned patents, is colorless or slightly blue before ultraviolet light irradiation and becomes an intense blue color after irradiation. When (SO) derivatives are incorporated into a plastic host material, such as cellulose acetate butyrate, (CAB), the resulting material shows this same photochromic behavior. A great deal of effort has been made to avoid this intense blue color. However, until the present invention, this effort has failed as evidenced by the intense blue color shown in all of the compounds disclosed in the above-mentioned patents.

It was also found that with some of the (SO) derivative compounds of the above-mentioned patents there is a large thermal equilibration toward the colored form. Thus, when these particular (SO) compounds are incorporated into a plastic host, the resulting structure exhibits a low luminous transmittance in the unactivated state (before ultraviolet light irradiation), which renders these compounds undesirable for applications such as in lenses which go from a clear to a colored form. When an ultraviolet stabilizer is used with these (SO) derivative compounds, as disclosed in U.S. Pat. No. 4,440,672, the light fatigue resistance of the (SO) dye is improved without hindering the photocolorability of the photochromic composition. Improvement of the light fatigue resistance is desirable in order to broaden the use of a photochromic article and to increase its useful lifetime.

Accordingly, it is a principal object of the present invention to provide a new class of photochromic (SO) derivative compounds which are more neutral in color after being subjected to ultraviolet light irradiation.

It is another object of the present invention to provide a new class of photochromic (SO) derivative compounds, which when incorporated into a plastic host, will produce a photochromic material with a high luminous transmittance in the unactivated state, yet which can be darkened significantly when subjected to ultraviolet light irradiation.

Yet another object is to improve the light fatigue resistance of photochromic (SO) derivative compounds of the present invention without hindering their photocolorability, by employing an ultraviolet stabilizer.

It is a further object of the present invention to incorporate such improved photochromic (SO) derivative compositions into host materials and to fabricate photochromic articles such as sunglasses, ophthalmic lenses, ski goggles, window coatings, and the like, from the resulting photochromic material.

SUMMARY OF THE INVENTION

The problems of the prior art are overcome by the discovery of a novel class of organic photochromic compounds which maintain a more neutral color when subjected to ultraviolet light irradiation. These compounds are different from prior art (SO) compounds in that there is a substitution of a trifluoromethyl group in the indoline portion of the (SO) melecule.

When incorporated into a plastic host, such as cellulose acetate butyrate (CAB), the organic photochromic compounds of the present invention produce a plastic material which exhibits a high luminous transmittance in the unactivated state (before ultraviolet light irradiation), and which can be darkened significantly when subjected to ultraviolet light.

When an ultraviolet stabilizer is used with the (SO) dyes of the present invention, such as disclosed in U.S. Pat. No. 4,440,672, the light fatigue resistance of the photochromic composition is improved without hindering its photocolorability. By improving the light fatigue resistance, the useful life of the organic photochromic composition is also improved.

The organic photochromic compositions of the present invention may be incorporated within optically clear plastics to make a photochromic element suitable for photochromic sunglass lenses, ski goggles, ophthalmic lenses, window coatings, and the like. They may also be incorporated into opaque plastic materials suitable for use in toys and other articles to impart photochromic properties in such articles.

DESCRIPTION OF THE PREFERRED EMBODIMENT

Figure 1:
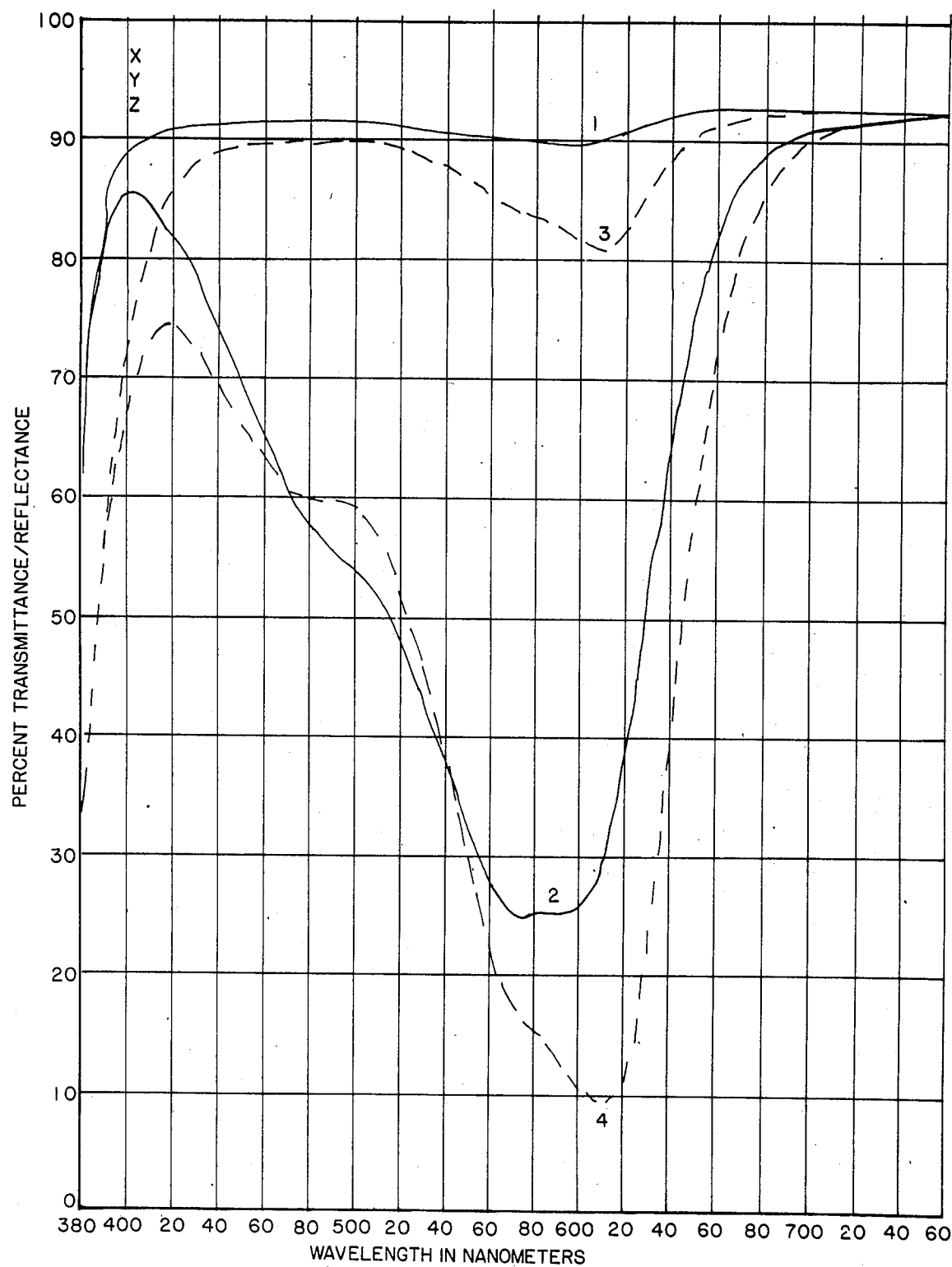
FIG. 1 illustrates the transmission spectrum of 4- and 6-trifluoromethyl-1,3,3-trimethyl-9'-methoxy (SO) and 1,3,3,4,5(and 5,6)-pentamethyl-9'-methoxy (SO) compound in CAB before and after ultraviolet light irradiation.

At the outset the invention is described in its broadest overall aspects with a more detailed description following.

The organic photochromic composition of the present invention comprises spiro (indoline-2,3'-(3H)-napth-(2,1-b)(1,4) oxazine) (SO) dye, of the formula

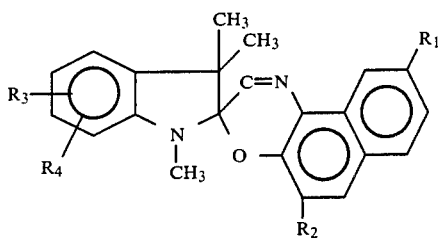

wherein one of $R_1$ and $R_2$ is a lower alkoxy group and the other is hydrogen; $R_3$ is a trifluoromethyl group; and $R_4$ is hydrogen, a lower alkyl or a lower alkoxy group. $R_3$ and $R_4$ are independently located at the 4,5,6, or 7 position of the indoline ring, although, of course, there can be only one substituent at any one position. By lower alkyl or lower alkoxy is meant a moiety containing 1 to 4 carbon atoms.

When the organic photochromic composition of the present invention is to be incorporated into a plastic host, the preferred class of compounds comprises a lower alkoxy group at $R_1$ or $R_2$ and most preferably methoxy or ethoxy, trifluoromethyl at $R_3$, and hydrogen or methyl at $R_4$. This gives the resulting photochromic plastic material a high luminous transmittance in the unactivated state (before ultraviolet irradiation), which can be darkened significantly in the presence of ultraviolet light irradiation.

In accordance with the present invention, the preferred (SO) dyes are:

4-trifluoromethyl-1,3,3-trimethyl-5'-methoxy spiro (indoline-2,3'-(3H)-napth-(2,1-b)(1,4)oxazine);

6-trifluoromethyl-1,3,3-trimethyl-5'-methoxy spiro (indoline-2,3'-(3H)-napth-(2,1-b)(1,4)oxazine);

4-trifluoromethyl-1,3,3-trimethyl-9'-methoxy spiro (indoline-2,3'-(3H)-naphth-(2,1-b)(1,4) oxazine);

6-trifluoromethyl-1,3,3-trimethyl-9'-methoxy spiro (indoline-2,3'-(3H)-napth-(2,1-b)(1,4) oxazine);

5-trifluoromethyl-1,3,3-trimethyl-9'-methoxy spiro (indoline-2,3'-(3H)-napth-(2,1-b)(1,4) oxazine);

$Y_1$-trifluoromethyl-$Y_2$-methyl-1,3,3-trimethyl-9'-methoxy spiro (indoline-2,1'-(3H)-napth-(2,1-b)(1,4) oxazine);

4-trifluoromethyl 1,3,3-trimethyl-5'-ethoxy spiro (indoline-2,3'-(3H)-napth-(2,1,b)(1,4) oxazine);

6-trifluoromethyl-1,3,3-trimethyl-5'-ethoxy spiro (indoline-2,3'-(3H)-napth-(2,1-b)(1,4) oxazine);

4-trifluoromethyl-1,3,3-trimethyl-9'-ethoxy spiro (indoline-2,3'-(3H)-napth-(2,1-b)(1,4) oxazine);

6-trifluoromethyl-1,3,3-trimethyl-9'-ethoxy spiro (indoline-2,3'-(3H)-napth-(2,1-b)(1,4) oxazine;

$Y_1$-trifluoromethyl-$Y_2$-methyl-1,3,3-trimethyl-5'-methoxy spiro (indoline-2,3'-(3H)-napth-(2,1-b)(1,4) oxazine).

Reference to $Y_1$ and $Y_2$ indicates attachment at the 4, 5, 6 or 7 position, although both cannot be at the same position, but the exact position was not determined.

To enhance the light fatigue resistance of the organic photochromic material of the present invention, without affecting its photocolorability, it is preferable to add an ultraviolet stabilizer belonging to the class of peroxide decomposers or the class of excited state quenchers, preferably a singlet oxygen quencher, and most preferably a complex of $Ni^{2+}$ ion with an organic ligand. These $Ni^{2+}$ complexes are normally used in polyolefins to provide protection from photodegradation. The ultraviolet stabilizers used in the present invention will not hinder the photocolorability of the (SO) dyes, because they have a minimal absorption in the ultraviolet region where (SO) dyes absorb. Improving the light fatigue resistance also improves the useful life of the organic photochromic compositions of the present invention.

Preferably, between 0.01 and about 15% by weight of the (SO) dye and between 0.1 and about 5% by weight of the ultraviolet stabilizer, depending on its solubility, is incorporated into an optically clear plastic material having enhanced light fatigue resistance. The optically clear matrix will preferably have a thickness in the range of 0.0001–2.0 inch. As used throughout this specification and claims, all percentages are by weight unless otherwise specified.

In another important embodiment, the (SO) dye and ultraviolet stabilizer is mixed in solution with an optically clear pre-polymer liquid which is thereafter cast as a film or lens, or otherwise incorporated into a polymer which is injection molded or shaped into a film or lens; or a prepolymerized film or lens containing the ultraviolet stabilizer may be immersed in a dye bath comprising (SO) dye dissolved in a solution of organic solvents such as alcohol, toluene, halogenated hydrocarbon or the like. Other methods of blending the ultraviolet stabilizer with the (SO) dye and optically clear polymer, such as coating or laminating may also be employed.

Ultraviolet stabilizers useful herein include complexes of $Ni^{2+}$ ion with some organic ligand, cobalt (III) tri-di-n-butyldithiocarbamate, and cobalt (II) di-iso-propyldithiocarbamate.

The preferred ultraviolet stabilizers are $Ni^{2+}$ complexes and more particularly (2,2'-thiobis(4-(1,1,3,3-tetramethylbutyl) phenolato)(butylamine) nickel

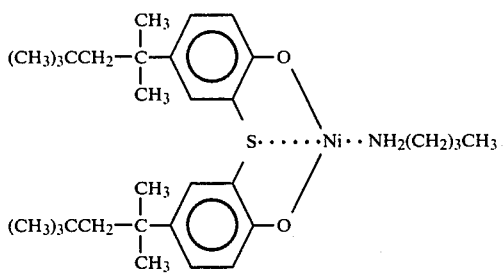

sold under the tradename of Cyasorb UV 1084, obtained from the American Cyanamid Company; nickel (0-ethyl(3,5-di-tert-butyl-4-hydroxybenzyl) phosphonate

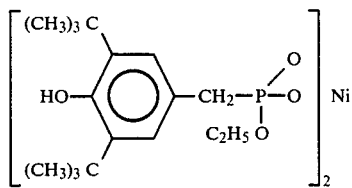

sold under the tradename of Irgastab 2002, obtained from the Ciba-Geigy Corporation; nickel dibutyldithiocarbamate

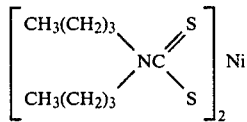

sold under the tradename of Rylex NBC, obtained from E. I. duPont de Nemours & Company; bis(2,2'-thiobis-4-(1,1,3,3-tetramethylbutyl)phenolato) nickel

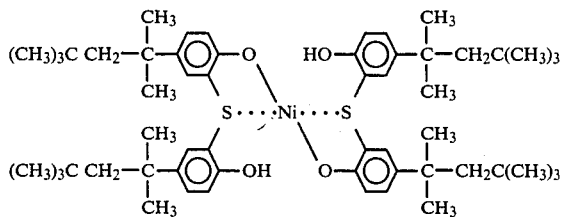

sold under the tradename of UV-Chek AM 101, obtained from the Ferro Corporation; nickel di-isopropyldithiophosphate (NIDIPDTP);

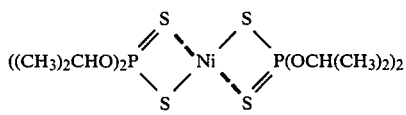

and other $Ni^{2+}$ complexes sold under the tradenames of UV-Chek AM 105, UV-Chek AM 126, and UV-Chek AM 205 which can also be obtained from the Ferro Corporation.

The preferred transparent plastic hosts are cellulose actate butyrate (CAB); CR-39 TM, a dithylene glycol bis(allylcarbonate) obtained from PPG Industries, Inc.; Lexan TM, a polycarbonate condensation product of bisphenol-A and phosgene, obtained from General Electric; and Plexiglas TM, a polymethyl methacrylate obtained from the Rohm and Haas Company. Other plastic materials into which the photochromic compositions of this invention may be incorporated include polyvinyl chloride, polyvinyl acetate, polystyrene, polyurethane, polyesters and epoxies. The invention is further illustrated by the following non-limiting examples (As used throughout the examples, the formula CF3 is intended to represent trifluoromethyl; the formula $CH_3O$ is intended to represent methoxy; and the formula $C_2H_5O$ is intended to represent ethoxy.)

EXAMPLES 1-5

A mixture of 22 grams of 1-nitroso-7-mthoxy-2-naphthol in 250 ml. of ethanol was bubbled with $N_2$ gas for 15 minutes before bringing it to a gentle reflux. A solution of 36.9 grams of a mixture of 4-and 6-trifluoromethyl-1,2,3,3-tetramethyl-indoleninium iodide isomers in 50 ml. of ethanol containing 12 grams of triethylamine was added ovr a period of 30 minutes. After the mixture was refluxed for two hours, the solution was then cooled and the resulting brown precipitate was separated by filtering. The crude produce was purified by recrystallization from actone. A set of photochromic compounds was synthesized in this manner using starting materials having the appropriate substituents. A list of these compounds is shown in Table I.

TABLE I

| List of Compounds Synthesized | |
|---|---|
| 1. $R_1$ = $CH_3O$<br>$R_2$ = H<br>$R_3$ = 4- & 6-$CF_3$ (mixture)<br>$R_4$ = H | 2. $R_1$ = $CH_3O$<br>$R_2$ = H<br>$R_3$ = 5-$CF_3$<br>$R_4$ = H |
| 3. $R_1$ = $C_2H_5O$<br>$R_2$ = H<br>$R_3$ = 4 & 6-$CF_3$ (mixture)<br>$R_4$ = H | 4. $R_1$ = H<br>$R_2$ = $CH_3O$<br>$R_3$ = 4- & 6-$CF_3$ (mixture)<br>$R_4$ = H |
| 5. $R_1$ = H<br>$R_2$ = $C_2H_5O$<br>$R_3$ = 4- & 6-$CF_3$ (mixture)<br>$R_4$ = H | |

EXAMPLES 6-7

Benzotrifluoride (29 gm) was added to a solution of butyl lithium (13.5 gm) in ether (250 ml) which was cooled by an ice-water bath, then this mixture was refluxed for 2 hours. After cooling, a solution of methyl iodide (35 gm) in ether (100 ml) was added slowly over a period of one hour. Subsequently, the mixture was refluxed for 8 hours and then distilled, with the fraction boiling in the range of 120°-128° C. collected. The yield was 19 gm of methyl-benzotrifluoride isomers.

To the methylbenzotrifluoride isomers (16 gm) cooled in an ice-water bath was slowly added a solution of concentrated nitric acid (20 ml) and concentrated sulfuric acid (20 ml) to keep $T \leq 55°$ C. The mixture was then stirred for 0.5 hours at 50° C., followed by vacuum distillation and collected at 105°-130° C.

The nitro-methylbenzotrifluoride isomer mixture (15 gm) in ethanol (300 ml) was hydrogenated at 20°-45° C. and 40 psi over Pd-on-carbon catalyst (0.1 gm) for 5-8 hours. The mixture was then distilled to give a mixture of amino-methylbenzotrifluoride isomers.

The desired ndolenium iodide isomers were obtained by the well known Fischer indole synthesis and the final (SO) dye was obtained as described in the Examples 1-5. The dyes prepared had the following substituent selection, wherein $Y_1$ and $Y_2$ indicate attachment at the 4,5,6 or 7 position, but the exact position of attachment was not determined.

| 6. $R_1 = CH_3O$ | 7. $R_1 = H$ |
|---|---|
| $R_2 = H$ | $R_2 = CH_3O$ |
| $R_3 = Y_1-CF_3$ | $R_3 = Y_1-CF_3$ |
| $R_4 = Y_2-CH_3$ | $R_4 = Y_2-CH_3$ |

EXAMPLES 8-14

A series of CAB films were cast in the thickness of 3.5 to 4.0 mils and contained two weight percent of photochromic compounds prepared in accordance with Examples 1-7. The films were colorless, but became an intense purplish-gray color upon exposure to ultraviolet light irradiation, in contrast to the deep blue color shown by the prior art compounds.

The positions of the main absorption peaks in the visible region of the spectrum of these CAB films after ultraviolet light irradiation are shown in Table II, which illustrates the substantial spectral shift induced by the substitution of a trifluoromethyl group in the indoline part of the molecule.

TABLE II
Position of the Absorption Peaks of the (SO) Compounds with a Trifluoromethyl Substituent

| Compounds | Positions (nm) |
|---|---|
| 4- & 6-CF$_3$—9'-CH$_3$O | 590, 570, 490 |
| 4- & 6-CF$_3$—5'-CH$_3$O | 570, 490 |
| 5-CF$_3$—9'-CH$_3$O | 600, 570, 490 |
| 4- & 6-CF$_3$—9'-C$_2$H$_5$O | 600, 570, 490 |
| 4- & 6-CF$_3$—5'-C$_2$H$_5$O | 575, 490 |
| $Y_1$—CF$_3$—$Y_2$—CH$_3$—9'-CH$_3$O | 580, 485 |
| $Y_1$—CF$_3$—$Y_2$—CH$_3$—5'-CH$_3$O | 600, 575, 490 |
| ($R_1$-$R_4$ = H) | 610, 570 (SH)* |

*Shoulder (not a complete peak)

Figure 2:
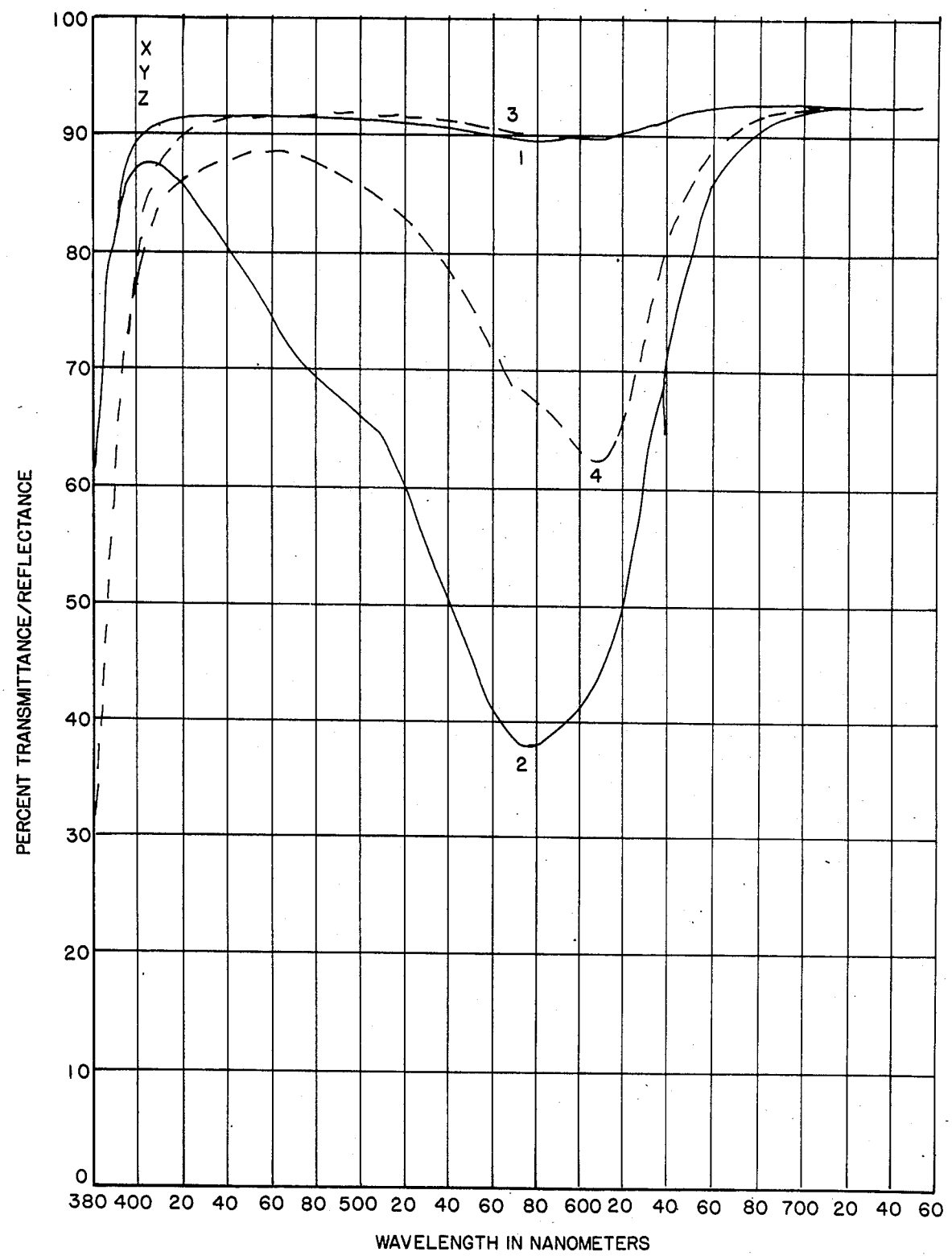
FIG. 2 illustrates the transmission spectrum of 4- and 6-trifluoromethyl 1,3,3-trimethyl-5'-methoxy (SO) and the parent compound in CAB before and after ultraviolet light irradiation.

As a further illustration, the activated spectrum of 4-and 6-trifluoromethyl-9'-methoxy, and 4- and 6-trifluoromethyl-5'-methoxy (SO) dyes are respectively compared to 1,3,3,4,5(and 5,6)-pentamethyl-9'methoxy (SO) and the unsubstituted parent (SO) compound in FIGS. 1 and 2 to demonstrate this large spectral shift induced by a trifluoromethyl substituent. Curves 1 and 2 are for the trifluoromethyl derivative and Curves 3 and 4 are for the pentamethyl compound ($R_1$=OCH$_3$, $R_2$=H, $R_3$ and $R_4$=CH$_3$) and the parent compound ($R_1$, $R_2$, $R_3$ and $R_4$=H).

EXAMPLES 15-21

A series of CAB films was cast in accordance with Examples 8-14. The luminous transmittance (L.T.), in percent, of the unactivated (before ultraviolet light irradiation) films was measured ad is shown in Table III. The data clearly indicates that the trifluoromethyl group greatly suppresses the initial coloration of 5'-methoxy derivative compounds and, hence, increases the usefulness of this particular class of (SO) derivatives.

TABLE III
Luminous Transmittance in Unactivated State

| Substituent(s) in Indoline | L.T. (%) |
|---|---|
| H (compound of prior art) | 67 |
| 5-Ch$_3$ (compound of prior art) | 50 |
| 5-CH$_3$O (compound of prior art) | 40 |
| 5-CL | 79 |

TABLE III-continued
Luminous Transmittance in Unactivated State

| Substituent(s) in Indoline | L.T. (%) |
|---|---|
| 4- & 6-CF$_3$ (mixture) | 90 |
| $Y_1$—CF$_3$—$Y_2$—CH$_3$ | 82 |
| 4- & -6-CF$_3$—5'-C$_2$H$_5$O | 87 |

EXAMPLES 22-26

A set of CAB films was cast from a 50 gram solution of 10% CAB in methylene chloride containing 100 mgs. 4-and 6-trifluoromethyl-9'methoxy (SO) isomer mixture and 50 mgs. of ultraviolet stabilizer Ni$^{2+}$ complexes (13 mgs of Rylex NBC). The Ni$^{2+}$ complexes used were (2,2'-thiobis(4-(1,1,3,3-tetramethylbutyl)phenolato)(-butylamine) nickel (sold under the tradename of Cyasorb UV 1084 and obtained from the American Cyanamid Company); a Ni$^\circ$+ complex sold under the tradename of UV-Chek AM-105 and obtained from the Ferro corporation; a Ni$^{2+}$ complex sold under the tradename of UV-Chek AM-126 and obtained from the Ferro Corporation; and nickel dibutyldithiocarbamate (sold under the tradename of Rylex NBC and obtained from E. I. duPont de Nemours & Company. A control without the Ni$^{2+}$ complexes was also cast.

These five CAB films were subjected to 20-hour cycle exposures in a Fadeometer manufactured by Atlas Electric Devices of Chicago, Ill. After three 20-hour cycles of Fadeometer exposure, the control lost all of its photochromism. As shown in Table IV, the CAB films compounded with the Ni$^{2+}$ complexes still showed good photochromism.

TABLE IV
Residual Photocolorability of CAB Films after 60 Hours of Fadeometer Exposure

| Compound | Residual Photocolorability (%) |
|---|---|
| Cyasorb UV 1084 | 87 |
| UV-Chek AM-105 | 78 |
| UV-Chek AM-126 | 76 |
| Rylex NBC | 95 |
| Control | 0 |

While the invention has been described with reference to its preferred embodiment, other embodiments can achieve the same results. Variations and modifications of the present invention will be obvious to those skilled in the art and it is intended to cover in the appended claims all such modifications and equivalents as follows in the true spirit and scope of this invention.

I claim:

1. An organic photochromic composition comprising at least one photochromic compound having the structural formula:

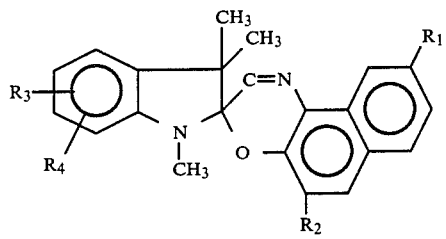

wherein one of $R_1$ and $R_2$ is a lower alkoxy group and the other is hydrogen; $R_3$ is a trifluoromethyl group;

and R4 is hydrogen, a lower alkyl or a lower alkoxy group.

2. An organic photochromic composition comprising: at least one photochromic compound having the structural formula:

[Chemical structure showing indoline-naphthoxazine compound with substituents $R_1$, $R_2$, $R_3$, $R_4$ and CH$_3$ groups]

wherein one of $R_1$ and $R_2$ is a lower alkoxy group and the other is hydrogen; $R_3$ is a trifluoromethyl group; and $R_4$ is hydrogen, a lower alkyl or a lower alkoxy group; and an ultraviolet stabilizer belonging to the class of peroxide decomposers or the class of excited state quenchers.

3. The composition of claim 2 wherein the ultraviolet stabilizer comprises a singlet oxygen quencher.

4. The composition of claim 3 wherein the singlet oxygen quencher comprises a complex of $Ni^{2+}$ ion with an organic ligand.

5. The composition of claim 4 wherein the $Ni^{2+}$ complex comprises (2,2'-thiobis-4-(1,1,3,3-tetramethylbutyl)phenolato)(butylamine) nickel.

6. The composition of claim 4 wherein the $Ni^{2+}$ complex comprises nickel (0-ethyl(3,5-di-tert-butyl-4-hydroxybenzyl) phosphonate.

7. The composition of claim 4 wherein the $Ni^{2+}$ complex comprises nickel dibutyldithiocarbamate.

8. The composition of claim 4 wherein the $Ni^{2+}$ complex comprises bis(2,2'-thiobis-4-(1,1,3,3-tetramethylbutyl)phenolato) nickel.

9. The composition of claim 4 wherein the $Ni^{2+}$ complex comprises nickel di-isopropyldithiophosphate.

10. The composition of claim 3 wherein the singlet oxygen quencher comprises cobalt (II) di-iso-propyldithiocarbamate.

11. The composition of claims 1 or 2 wherein $R_1$ is methoxy or ethoxy, $R_2$ is hydrogen, $R_3$ is trifluoromethyl and $R_4$ is hydrogen.

12. The composition of claims 1 or 2 wherein $R_1$ is hydrogen, $R_2$ is methoxy or ethoxy, $R_3$ is trifluoromethyl and $R_4$ is hydrogen.

13. The composition of claims 1 or 2 wherein $R_1$ is methoxy or ethoxy, $R_2$ is hydrogen, $R_3$ is trifluoromethyl and $R_4$ is methyl.

14. The composition of claims 1 or 2 wherein $R_1$ is hydrogen, $R_2$ is methoxy or ethoxy, $R_3$ is trifluoromethyl and $R_4$ is methyl.

15. The composition of claims 1 or 2 wherein the photochromic compound is selected from 4-trifluoromethyl-1,3,3-trimethy-5'-methoxy spiro (indoline-2,3'-(3H)-naphth-(2,1-b)(1,4) oxazine), 6-trifluoromethyl-1,3,3-trimethyl-5'-methoxy spiro (indoline-2,3'-(3H)-naphth-(2,1-b) (1,4) oxazine), 4-trifluoromethyl-1,3,3-trimethyl-9'-methoxy spiro (indoline-2,3'-(3H)-naphth-(2,1-b)(1,4) oxazine), 6-trifluoromethyl-1,3,3-trimethyl-9'-methoxy spiro (indoline-2,3'-(3H)-naphth-(2,1-b)(1,4) oxazine), 4-trifluoromethyl-1,3,3-trimethyl-9'-ethoxy spiro (indoline-2,3'-(3H)-naphth-(2,1-b)(1,4) oxazine), 6-trifluoromethyl1,3,3-trimethyl-9'-ethoxy spiro (indoline-2,3'-(3H)-naphth-(2,1-b)(1,4) oxazine), 4-trifluoromethyl-1,3,3-trimethyl-5'-ethoxy-spiro (indoline-2,3'-(3H)-naphth-(2,1-b)(1,4) oxazine), 5-trifluoromethyl-1,3,3-trimethyl-5'-ethoxy spiro (indoline-2,3'-(3H)-naphth-(2,1-b)(1,4)oxazine), and mixtures thereof.

16. A photochromic article comprising:
(a) a plastic host; and
(b) at least one photochromic compound incorporated into said host having the structural formula:

[Chemical structure showing indoline-naphthoxazine compound with substituents $R_1$, $R_2$, $R_3$, $R_4$ and CH$_3$ groups]

wherein one of $R_1$ and $R_2$ is a lower alkoxy group and the other is hydrogen; $R_3$ is a trifluoromethyl group; and $R_4$ is hydrogen, a lower alkyl or a lower alkoxy group.

17. A photochromic article comprising:
(a) a plastic host; and
(b) at least one photochromic compound incorporated into said host having the structural formula:

[Chemical structure showing indoline-naphthoxazine compound with substituents $R_1$, $R_2$, $R_3$, $R_4$ and CH$_3$ groups]

wherein one of $R_1$ and $R_2$ is a lower alkoxy group and the other is hydrogen; $R_3$ is a trifluoromethyl group; and $R_4$ is hydrogen, a lower alkyl or a lower alkoxy group; and
(c) an ultraviolet stabilizer incorporated into said host belonging to the class of peroxide decomposers or the class of excited state quenchers.

18. The photochromic article of claim 17 wherein the ultraviolet stabilizer comprises a singlet oxygen quencher.

19. The photochromic article of claim 18 wherein the singlet oxygen quencher comprises a complex of $Ni^{2+}$ ion with an organic ligand.

20. The photochromic article of claim 18 wherein the singlet oxygen quencher comprises cobalt (II) di-iso-propyldithiocarbamate.

21. The photochromic article of claims 16 or 17 wherein the host is cellulose acetate butyrate.

22. The photochromic article of claims 16 or 17 wherein the host is polycarbonate resin.

23. The photochromic article of claims 16 or 17 wherein the host is polymethylmethacrylate.

24. The photochromic article of claims 16 or 17 wherein the host is diethylene glycol bis(allyl carbonate).

25. The photochromic article of claim 16 or 17 wherein the photochromic compound comprises a mixture of 4- and 6-trifluromethyl 1,3,3-trimethyl-5'- methoxy spiro (indoline-2,3'-(3H)-naphth-(2,1-b)(1,4)oxazine).

26. The photochromic article of claims 16 or 17 wherein the photochromic compound comprises a mixture of 4-and 6-trifluoromethyl-1,3,3-trimethyl-9'-methoxy spiro (indoline-2,3'-(3H)-naphth-(2,1-b)(1,4)oxazine).

27. The photochromic article of claims 16 or 17 wherein the photochromic compound comprises a mixture of 4- and 6-trifluoromethyl-1,3,3-trimethyl-5'-ethoxy spiro (indoline-2,4'-(3H)-naphth-(2,1-b)(1,4) oxazine).

28. The photochromic article of claims 16 or 17 wherein the photochromic compound comprises a mixture of 4- and 6-trifluoromethyl 1,3,3-trimethyl-9'-ethoxy spiro (indoline-2,3'-(3H)-naphth-(2,1-b)(1,4) oxazine).

29. The photochromic article of claim 16 or 17 wherein the photochromic compound comprises 5-trifluoromethyl-1,3,3-trimethyl-9'-methoxy spiro (indoline-2,3'-(3H)-naphth-(2,1-b)(1,4)oxazine).

30. The photochromic article of claims 16 or 17 wherein the photochromic compound comprises $Y_1$-trifluoromethyl-$Y_2$-methyl-1,3,3-trimethyl-5'-methoxy spiro (indoline-2,3'-(3H)-naphth (2,1-b)(1,4) oxazine), wherein $Y_1$ and $Y_2$ indicates attachment at the 4,5,6, or 7 position.

31. The photochromic article of claims 16 or 17 wherein the photochromic compound comprises $Y_1$-trifluoromethyl-$Y_2$-methyl-1,3,3-trimethyl-9'-methoxy spiro (indoline-2,3'-(3H)-naphth (2,1-b)(1,4) oxazine), wherein $Y_1$ and $Y_2$ indicates attachment at the 4,5,6 or 7 position.

32. The photochromic article of claim 17 wherein the article is a lens.

* * * * *